(12) United States Patent
Seitz et al.

(10) Patent No.: US 7,048,951 B1
(45) Date of Patent: *May 23, 2006

(54) SYSTEMS AND METHODS FOR TOPICAL TREATMENT WITH NITRIC OXIDE

(75) Inventors: William A. Seitz, Dickinson, TX (US); Robert E. Garfield, Friendswood, TX (US); Alexandru T. Balaban, Columbia, MD (US); Randall J. Stewart, Galveston, TX (US)

(73) Assignee: Nioxx, LLC, Dickinson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/296,110

(22) PCT Filed: May 24, 2000

(86) PCT No.: PCT/US00/14239

§ 371 (c)(1),
(2), (4) Date: Nov. 22, 2002

(87) PCT Pub. No.: WO01/89572

PCT Pub. Date: Nov. 29, 2001

Related U.S. Application Data

(63) Continuation-in-part of application No. 09/095,174, filed on Jun. 10, 1998, now Pat. No. 6,103,275.

(51) Int. Cl.
*A61K 33/00* (2006.01)

(52) U.S. Cl. .................. 424/718; 514/474; 514/458; 514/578

(58) Field of Classification Search .............. 424/718; 514/474, 458, 578
See application file for complete search history.

(56) References Cited

U.S. PATENT DOCUMENTS 6,103,275 A * 8/2000 Seitz et al. .................. 424/718

OTHER PUBLICATIONS

Tucker et al, Lancet, vol. 354, #9191, pp. 1670–75 (Nov. 1999).*

* cited by examiner

*Primary Examiner*—James H Reamer
(74) *Attorney, Agent, or Firm*—Jackson Walker L.L.P.

(57) ABSTRACT

A simple, biocompatible system and procedure for generating nitric oxide (NO) is described. A mixture of powdered sodium nitrite, ascorbic acid, and maleic acid (or another organic acid of adequate strength) immediately generates nitric oxide (NO) on treatment with water. To slow down the NO generation, one may prepare an ointment from a non-aqueous medium (petrolatum, Vaseline™) and the three powdered ingredients, which on being applied topically on the skin will release NO as water permeates through this medium; alternatively, one may convert the aqueous sodium nitrite solution into a gel with hydroxyethylcellulose (or other gel-forming compound) and combine this gel with another gel obtained from aqueous ascorbic and maleic acids with hydroxyethylcellulose for topical application (on intact skin, burns intra-cavity, burns, intra-cavity, etc.). The two gels may be admixed immediately before use (possibly from a single container with separate chambers and dual nozzle, via pushing or squeezing the two gels through the nozzle), or may be applied in sandwich-like fashion (possibly as a transdermal patch) for further slowing down the delivery of NO.

35 Claims, 7 Drawing Sheets

Time for 50% Healing

Time for 50% Healing

SYSTEMS AND METHODS FOR TOPICAL TREATMENT WITH NITRIC OXIDE

This is a CIP of Ser. No. 09/095,174 filed Jun. 10, 1998 and issued Aug. 15, 2000 as U.S. Pat. No. 6,103,275.

BACKGROUND OF THE INVENTION

The present invention relates generally to the fields of tissue malfunction remedies. More particularly, it concerns application of a new nitric oxide-generating mixture to accelerate tissue healing or reduce undesired tissue contractions.

The biological importance of NO is well documented (Lancaster, 1996; Vincent, 1995; Moncada et al., 1992–1994; Feelisch and Stamler, 1996; Williams, 1996; Butler and Williams 1993; Ignarro and Murad, 1995). In mammals, NO is an endogenous physiological mediator of many biological functions. In addition, it is applied pharmacologically in various forms usually referred to as NO donors (nitroglycerin, sodium nitroprusside, etc.) to correct NO deficient states or to regulate the activities of many tissues (see appended list). Topical applications may be used to help wound and burn healing, hair growth, impotence, and cause vasodilatation where needed (e.g., ripening of the cervix in pregnancy). Local higher concentrations of NO (eye, skin, e.g.) are tolerated. Smith et al. (U.S. Pat No. 5,519,020) describe polymeric nitric oxide sources thought to be useful to promote healing.

Two types of NO synthases (inducible and constitutive) produce NO in living organisms from L-arginine. Synthetic NO donors are also of two different types: those that evolve spontaneously NO as such from chemical precursors (Keefer et al., 1994; Keefer et al., 1993, U.S. Pat. No. 5,212,204; Hansen et al., 1992; Keefer et al., 1996; Garfield et al., 1995, U.S. patent application Ser. No. 08/440,970) or from solutions in suitable solvents (Garfield et al., 1996, U.S. patent application Ser. No. 08/633,337), and those that need metabolic redox processes for releasing NO (usually from higher oxidation states). Among the latter ones, organic nitrates (glycerol trinitrate (trivially known as nitroglycerin), isosorbide dinitrate or organic nitrites have been long used in medicine but they are known to produce tolerance, i.e., the need to progressively increase the dose in order to obtain a constant effect. These are also known to produce undesirable systemic side effects (e.g., headache).

Colorless gaseous NO (under some conditions) may react rapidly with atmospheric oxygen, yielding nitrogen dioxide ($NO_2$), a red-brown gas with much higher toxicity than NO. However, at very low concentrations (up to 0.1 parts per million in air), NO may be administered to humans having breathing problems and have beneficial effects due to its bronchodilatory and vasodilatory activity. The reason why the reaction rate of NO with oxygen is very low at minute concentrations is related to the fact that the square of the NO concentration enters the expression of the reaction rate, according to the stoichiometry (eq. 1):

$$2NO + O_2 \rightarrow 2NO_2 \quad (1)$$

Nitrous acid ($pK_a = 3.37$) is produced from inorganic nitrites on treatment with acids (HA) of higher or comparable strength in the literature, hydrochloric acid is described for this purpose (Feelisch and Stamler, 1996). Nitrous acid is stable in aqueous solution at low temperature, but it decomposes into NO and $NO_2$ readily at room temperature according to the equations (2) and (3):

$$2HA + 2NaNO_2 \rightarrow 2HNO_2 + 2NaA \quad (2)$$

$$2HNO_2 \rightarrow NO + NO_2 + H_2O \quad (3)$$

There is, under the current U.S. Department of Agriculture regulations, the specification that for curing meat (especially ham and canned meat) and imparting a pink color to it, sodium nitrite must be used in combination with reducing agents such as ascorbate, erythrobate, or α-tocopherol (USDA *Federal Registry*, 1978; Mirvish, *Appl. Pharmacol.*, 1975; Cornforth, 1996). Also, the literature specifies that sodium ascorbate has a beneficial effect, again for use in meat products (Reith and Szakali, 1967). It is conjectured that nitric oxide is the active agent in these meat-curing processes, and that the color is due to the binding of nitric oxide to myoglobin. However, the above-mentioned uses antedate considerably the discovery of NO as an important physiological mediator, and until now the methods and procedures selected by the inventors are not described as a means for topical delivery of nitric oxide.

Uses and Potential Uses of Nitric Oxide (NO) include
- Cardiovascular: hypertension; angina; atherosclerosis; preeclampsia (pregnancy induced hypertension; toxemia; eclampsia; HELP syndrome; regulation of vascular conductance; regulation of blood flow; regulation of blood pressure; and myocardial ischemia.
- Gastrointestinal: altered motility; and pyloric stenosis.
- Lung Function: asthma; treatment of premature babies to increase lung function; and pulmonary hypertension.
- Inflammation: autoimmune and immune diseases; acute inflammation; arthritis; resistance to infection; cancer, SLE—Lupus; anaphylactic reactions; and allograft rejection.
- Central Nervous System: behavior; epilepsy; Alzheimer's disease; stroke; and growth hormone disorders (e.g., acromegaly).
- Pancreas: diabetes.
- Female Reproductive System or problems: ovulation; implantation/in vitro fertilization; premenstrual syndrome; dysmenorrhea; uterine contractile disorders; premature labor, cervical dilation; contraception; menopause symptoms; osteoporosis; endocrine disorders; and hormone replacement therapy.
- Male Reproductive Problems: impotence; penile erection; male menopause symptoms; endocrine disorders; osteoporosis; and prostate hypertrophy.
- Bladder and Kidney Problems: incontinence; renal arterial stenosis; and hypertension
- Dermatological Problems: eczema (skin reaction to foreign particle); autoimmune skin diseases; topical hair loss; acne; wounds; and burns.

The present invention includes formulations and methods for treating many, if not all, of these problems.

SUMMARY OF THE INVENTION

In one important aspect the present invention concerns a method for generating medically applicable nitric oxide. This method comprises combining a nitrite salt, a reductant and a mild acid. The mild acid has sufficient acidity (pKa between about 1 and about 4) to cause degradation of the nitrite to nitric oxide. These components are combined in a diffusion inhibiting medium which controls the rate of nitric oxide release and is sufficiently viscous to topically apply. While ascorbic acid or an ascorbate salt is preferred, other acceptable reductants such as erythrobate or α-tocopherol, for example, may be used.

The present invention, in one important aspect, involves a composition for generating and controlling the release rate of nitric oxide for topical applications that involves more than one gel. In this case, the first aqueous gel comprises a nitrite salt and a second aqueous gel comprises an acid with sufficient acidity to degrade the nitrite salt to nitric oxide. A reductant to help retain the nitric oxide in bioactive form is preferably included in the first or second gel. The acid is preferably an organic acid such as maleic acid, e.g., although inorganic acids such as boric acid, for example may also be suitable. Gellification agents include substances such as hydroxymethyl cellulose, gelatin, agar, and silicic acid, for example. One preferable nitrite salt is sodium nitrite, although others will also be usable. One preferred reductant is ascorbic acid (vitamin C). An acid agent may also be a reductant, such as ascorbic acid or an ascorbic acid variant with a lower pKa, for example. In one aspect, the first and second gels may be combined in layers with the nitrite-containing gel preferably in contact with skin. Prior to application these gels could be separated by an impermeable plastic or metal foil if desired. They could be applied directly to the skin or with an interposed gas-permeable membrane present to avoid possible skin irritation. The aqueous gels may be prepared in isotonic saline solutions and kept sterile prior to use. The topical application includes, of course, application to the skin and may also include any intracavitary application desired. A mixture of powdered sodium nitrite, ascorbic acid, (or other reductant) and maleic acid (or another organic acid of adequate strength) immediately generates nitric oxide (NO) on treatment with water. To slow the NO generation, one may prepare an ointment from a nonaqueous medium (petrolatum, Vaseline, e.g.) and the three powdered ingredients, which, on being applied topically on the skin, will release NO as water permeates through this medium. Alternatively, one may convert the aqueous sodium nitrite solution into an aqueous gel with hydroxyethylcellulose (or other gel-forming substance or compound) and combine this gel with another gel obtained from aqueous ascorbic and maleic acids with hydroxyethylcellulose for topical application (on intact skin, burns, intra-cavity, etc.). The two gels may be admixed immediately before use (possibly from a single container with separate chambers and dual nozzle, via pushing or squeezing the two gels through the nozzle of a device, see e.g., FIG. 7), or may be applied in sandwich-like fashion (possibly as a transdermal patch) for further slowing down the delivery of NO.

In one aspect the present invention involves therapeutically applying NO (nitric oxide) by a method comprising combining a nitrite salt, a biocompatible reductant and an acid with a pK between about 1 and about 4 in a medium and topically applying the combination to a body site. This method for the topical delivery of nitric oxide may be accomplished by steps comprising mixing a powdered nitrite salt with a powdered reductant and an acid having a pKa between about 2 and about 4 in a diffusion-inhibiting, topically applicable medium. The medium is then applied in an effective amount to a desired body site. The diffusion-inhibiting characteristic is a certain measure of viscosity or gellation such that the reaction between the nitrite salt and acid is slowed and controlled for a prolonged release of nitric oxide. Such a medium also is helpful in topical application, for example, to the skin or other body surface. Various nitrite salts may be used, most commonly inorganic ones such as sodium nitrite, although potassium nitrite, calcium nitrite, or any alkali or alkali earth nitrite should be usable. The preferred reductant is one having the reductive capability of preventing or slowing the oxidation of nitric oxide to nitrous oxide. Preferred reductants include ascorbic acid tocopherol, ascorbate salts, erythrobates or alpha-tocopherol. Other acceptable reductants are well known to those of skill in the arts. Sometimes the acid, particularly if it is an organic acid, may also be a reductant. Ascorbic acid, although slightly weaker an acid than desired for optimal nitric oxide release and control does have reductive characteristics and may be used under some circumstances as being both a reductant and an acid. Maleic acid is one preferred organic acid which is acceptable. Inorganic acids with the appropriate pKs should be acceptable, particularly if they are biologically acceptable (e.g. boric acid). The medium for dissolution of a nitrite and acid and/or reductant may be an aqueous medium or, in fact, a nonaqueous medium. Aqueous media are generally preferred and readily prepared as gels, although organic salves may also be usable under some circumstances. Methods for the application of these materials to a desired area are manifold, some of which are mentioned here and include applying a nitrite-containing gel or salve layer to the skin or other body site. This would be followed by overlaying a layer of acid and/or reductant. This should give rise to a controlled rate of nitric oxide release to contact the desired bodily surface. These can be manually applied or can be applied as premeasured layers. In some cases the gels may simply be mixed just prior to application to form a relative homogeneous but diffusion-inhibiting salve or gel with all components mixed therein and a sufficiently slow and controlled rate of nitric oxide generation.

Aqueous gelling agents usable in the methods of the present invention include agars, hydroxyethyl celluloses and many other materials known to those of skill in the art usable in preparing aqueous-based gels. The appropriate gels may be prepared in advance and packaged separated by an impermeable plastic or metal layer, meant to be removed just before use. After removal the layers may be topically applied, the nitrite-containing layer being preferably applied closest to the body site. In some cases, it may be desirable to interpose a gas permeable membrane on the body site prior to the application of the gel or ointment nitric oxide source. This may lessen any skin irritation possibly resulting with certain individuals.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
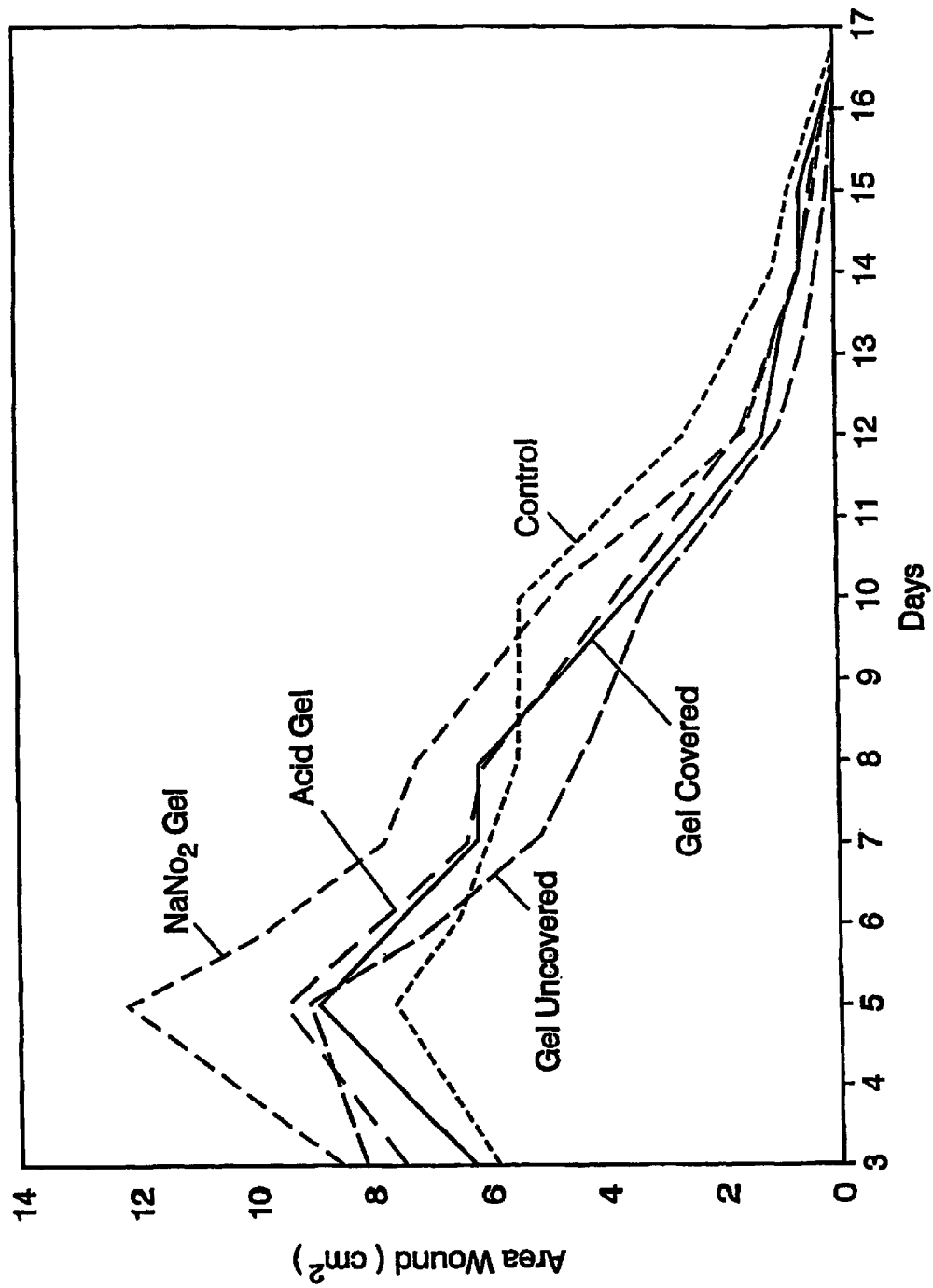
FIG. 1 gives the raw data for healing of second degree burns comparing control with covered and uncovered mixed gels (which release NO) and the individual acid or nitrite gels.

The present invention comprises a simple procedure for generating nitric oxide (NO) from water or biological fluids and a mixture of powdered biocompatible solid reagents, and also for converting aqueous solutions of such reagents into ointments or gels for topical application and slow delivery of NO. However, with reducing agents, only NO is produced, this constituting one of the main aspects of the present invention.

Biocompatible systems and procedures for generating nitric oxide (NO) are described herein that are particularly useful for topical applications.

Ascorbic acid (vitamin C) is one preferred biocompatible reducing agent for nitrites; its $pK_a$ is 4.10, making it a slightly weaker acid than nitrous acid. An acid with a pKa between about 1 and about 4 is preferred for NO generation, maleic acid being particularly preferred. Maleic acid ($pK_a$= 1.83 for the first ionization step) is about 30 times stronger than nitrous acid, is a crystalline solid without water of crystallization, and its salts are also tolerated biologically; many medicinal drugs with aliphatic amino groups are administered as maleates.

The methods described herein include mixing an aqueous solution of sodium nitrite with an aqueous solution of an equimolar amount of maleic acid, in the presence of an excess of ascorbic acid. The sodium nitrite is preferably kept separately from the other two ingredients because even ascorbic acid alone slowly generates NO if admixed with sodium nitrite.

The originality and advantages of the present procedure in one preferred embodiment include employing three safe and inexpensive compounds with convenient characteristics for producing NO free of any other residue that may cause adverse biological effects (as is potentially the case of many newly synthesized NO donors), and also free from the need of enzymatic reactions that may lead to tolerance (as is the case of organic nitrates functioning as NO donors). The composition of the mixture selected by the inventors is inventive, because so for no composition has been marketed or used that consists of (i) a nitrite salt with (ii) an organic acid of adequate strength and (iii) a reducing agent, all three ingredients being biocompatible. Few organic or other acids of the necessary strength are biologically tolerated, and in the absence of a reducing agent such as ascorbic acid the deleterious nitrogen dioxide could also be produced along with NO, as seen in eq. (3). One may therefore assert that the method and procedure described herein are unique in terms of the necessity of having the three types of ingredients selected by the inventors, and among representatives of these types the inventors have selected preferred ones.

Exemplary NO-releasing gels have been employed with two gelling agents:

1. hydroxyethylcellulose obtained from ethylene oxide (oxirane) and cellulose with definite molecular weights, lower than that of natural cellulose; and
2. poloxamer (Pluronic), a block copolymer of poly (ethylene glycol) and poly(propylene glycol).

Both of these particular types of gelling agents are non-ionic surfactants with hydrophobic and hydrophilic segments. In the case of hydroxyethylcellulose, the non-functionalized cellulose segments are water insoluble, having numerous hydrogen bonds between the parallel and linear β-glycosidic segments. On attaching hydroxyethyl groups, the corresponding glucose units become more hydrophilic. In the case of poloxamer, the poly (oxopropylene) segments are hydrophobic, whereas the poly (hydroxyethylene) segments are hydrophilic. The most interesting property of poloxamer gels in their non-Newtonian behavior, common to many types of polymers. The behavior on heating is opposite to that encountered with most other gelling agents such as gelatin: the fluidity of poloxamer gels increases on cooling and decreases on heating reversibly in the temperature range 0° C. to 50° C. The amount of Pluronic needed for gel formation is 2–3 times higher than that indicated for hydroxyethycellulose. Nitrite and acid-containing pluronic gels have been mixed and noted to cause skin reddening when mixed and applied thereto.

For references in this matter see:

I. R. Schmolka, Am. Perfum. Cosmet. 1967, 82, (7) 25–30.
I. R. Schmolka, "Polyalkylene Oxide Block Copolymers" in Nonionic Surfactants. M. Schick, Ed., Dekker, New York, 1967, pp. 300–371.
L. V. Allen Jr., "Compounding Gels", Secundum Artem, 1994,4 (5).

Many gels will not promote bacterial or mold growth, nor will they prevent it. Consequently, they need to be sterilized or contain preservatives. A number of preservatives and their concentrations that have been used in the preparation of such gels and more are well known to those of skill in the art. (See Table 1).

TABLE 1

Compatability of Selected Preservatives with Carbomer Gels

| Preservative | Concentration | Appearance | Compatible |
|---|---|---|---|
| Benzalkonium Chloride | 0.01% | Clear | Yes |
|  | 0.1% | Cloudy | No |
| Sodium Benzoate | 0.01% | Clear | Yes |
|  | 0.1% | Cloudy | No |
| Methylparaben | 0.18% | Clear | Yes |
| Propylparaben | 0.05% |  |  |
| Thiomersal | 0.01% | Clear | Yes |
|  | 0.1% | Clear | Yes |

In gel preparation, the powdered polymers, when added to water, may form temporary masses that slow the process of dissolution. As water diffuses into these loose clumps of powder, their exteriors frequently turn into clumps of solvated particles encasing dry powder. The blobs of gel may dissolve very slowly because of their high viscosity and low diffusion coefficient of the macromolecules.

As a hot, colloidal dispersion of gelatin cools, the gelatin macromolecules lose kinetic energy. With reduced kinetic energy, or thermal agitation, the gelatin macromolecules are associated through dipole-dipole interaction into elongated or threadlike aggregates. The size of these association chains increases to the extent that the dispersing medium is held in the interstices among the interlacing network of gelatin macromolecules, and the viscosity increases to that of a semisolid. Gums such as agar, Irish moss, algin, pectin and tragacanth, form gels by the same mechanism as gelatin.

Polymer solutions tend to cast gels because the solute consists of long, flexible chains of molecular thickness that tend to become entangled, attract each other by secondary valency forces, and even crystallize. Cross linking of dissolved polymer molecules also causes the solutions to gel. The reactions produce permanent gels, held together by primary valence forces. Secondary valence forces are responsible for reversible gel formation. For example, gelatin will form a gel when the temperature of a solution is lowered to about 30° C., the gel melting point. Lower temperatures, higher concentrations and higher molecular weights promote gelation and produce stronger gels. The reversible gelation of gelatin will occur at about 25° C. for 10% solutions, 30° C. for 20% solutions and about 32° C. for 30% solutions Gelation is rarely observed for gelatin above 34° C. and, regardless of concentration, gelatin solutions do not gel at 37° C. The gelation temperature or gel point of gelatin is highest at the isoelectric point. Water soluble polymers have the property of thermal gelation, i.e., they gel on heating, whereas natural gums gel on cooling. Thermal gelation is reversed on cooling. Some substances such as aqueous methyl cellulose solutions will gel when heated above the 50° C. because the polymer is less soluble in hot water and precipitates.

Inorganic salts will compete with the water present in a gel and cause gelation to occur at lower concentrations. This is usually a reversible process and, upon the addition of water, the gels will reform. Alcohol may cause precipitation or gelation because alcohol is a nonsolvent or precipitant, lowering the dielectric constant of the medium and tending to dehydrate the hydrophilic solute. Alcohol lowers the concentrations at which electrolytes salt out hydrophilic colloids. Phase separation by adding alcohol may cause coaceration.

Aqueous polymer solutions, especially of cellulose derivatives, are stored for approximately 48 hours after dissolution to promote full hydration, maximum viscosity and clarity. If salts are to be added, they are incorporated at this point rather than by dissolving in the water prior to adding the polymer. Otherwise the solutions may not reach their full viscosity and clarity.

Gels provide the pharmacist with an excellent drug delivery system for different routes of administration and are compatible with many different substances. Gels containing penetration enhances are especially popular for administering anti-inflammatory and anti-nauseant medications. They are relatively easy to prepare and are very efficacious.

A two gel method for delivery of NO will have the following properties. Dosage (total) can be controlled simply by adjusting the quantity of nitrite and acid. Rate can be independently controlled by adjusting the viscosity of the gel. Thus, a high total dosage can be delivered over a long period of time or a low total dosage can be delivered rapidly, as desired. In addition, various physical means for applying successive doses can be easily developed. For example, multilayer sandwiches could be formed with each successive layer activated by removing sequential barriers between gels (which themselves could even be of different strengths). Thus, a wound could remain covered for several treatments.

Another feature of the gels is that they are compatible with the addition of various agents such as sterilizing compounds and antibiotics, e.g.

Other mechanisms of application (other than topical) are possible. This technology might be used as sprays, suppositories, (aural, nasal, vaginal or rectal) or even injectable form to control many biological functions. It might also be dispensed in dropper form to be used in the eye, ear, nose or throat. Most of these applications deal with treatment of inflammation. The IV applications might be useful for acute angina and to regulate the cardiovascular system.

The gel might also be used in combination with various agents including antibiotics, anesthetics, analgesics, anti-inflammatory agents such as corticosteroids and nonsteroidal anti-inflammatory agents, antiviral agents, vasodilators or vasoconstrictors, sunscreen preparations (PABA), antihistamines, other hormones, such as estrogens, progesterone, androgens, antiseborretic agents, other cardiovascular agents, mast cell stabilizers, scabicides or pediculicides, keratolytics, lubricants, narcotics, shampoos, acne preparations, antiseborrheic agents, burn preparations, cleansing agents, deodorants, depiginenting agents, diaper rash products, emollients and moisturizers, photosensitizing agents, poison ivy or poison oak or sumac products, sunburn preparations, tar-containing preparations, wart preparations, wet dressings and wound care products. This would reduce any potential danger of infection introduced by the process.

The present gel technology is preferably but not necessarily a local NO delivery system as opposed to a systemic one. Therefore, the many systemic side effects of other NO treatments (such as nitroglycerin) should be completely avoided. This is an important advantage for a variety of problems.

A further advantage of the local application of the gels is that it is self regulating in the sense that when the desired effect of the treatment has been achieved, the remaining amount can simply be wiped off and the release stops. For subjects who might have some allergic response to other treatments, this ability to immediately stop treatment should be beneficial.

In addition to the list of uses and potential uses of NO, four important specific applications of the gel technology are worthy of more detailed discussion. These are generally related to the fact that the gels produce NO locally which in turn enhances local circulatory response.

Since topical application of the gels has been shown to immediately enhance local blood flow, the present gel technology can have important uses in treatments of male reproductive problems, especially penile erection and impotence. The ability to control dosage directly may be important here. Of course, if desired, antibiotics, spermicides and/or other additives may be included in such a gel.

Enhancement of local circulation is important for hair replacement and growth. The gel technology can be used to treat topical hair loss, particularly insofar as the hair loss is at least partially caused by microcirculation defects.

Burns respond to treatment with the gel as demonstrated in animal models—the results of which are included herein. Use of the gel technology in conjunction with other compounds may have application to even minor burns such as sunburn and other wounds.

NO donor compounds are important in the control of cervical dilation. The gel technology for this purpose is particularly appealing. First, it can be controlled directly and second, it is purely local as opposed to systemic.

There are numerous types of compounds which might be added to gels without unfavorably altering the NO donation properties but which would have some added features already known. These include antibiotics, steroids, antihistamines, antiinfective agents, prostaglandins, antipyretics, analgesics, anticycotics, antiseborrheic agents, anti psoriasis agents, antipruritics and local anesthetics. Also they may be combined with locally acing cardiovascular agents, e.g., alpha or beta blockers and Rogaine. Another type of compound which might be added to the gels is vasomax or other penile erectile agents. One can also combine the gels with vitamins, skin softeners, emollients, clearing agents, enzymes and keratolytics.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Experimental Procedure for Checking the Rapid Release of NO

Immediately before use a powdered combination of sodium nitrite (15 mmoles) and ascorbic acid (20 mmoles) is mixed magnetically with powdered maleic acid (20 mmoles) in a 500 ml four-necked flask connected (via ground-glass joints having stopcocks) to a vacuum pump, a manometer, an argon inlet, and a stoppered dropping funnel with pressure equalizer. After repeated evacuations and purgings with argon, water from the dropping funnel is admitted into the flask with stirring. A quantitative evolution of colorless NO with effervescence is observed by the pressure increase and corresponds to 15mmoles of NO. On admitting air into the flask until the pressure equalizes with atmospheric pressure, the red-brown color of $NO_2$ appears. The chemical reaction (4), where vitamin C is $Asc(OH)_2$ and maleic acid as MalH shows the reaction producing NO:

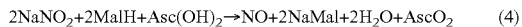

$$2NaNO_2 + 2MalH + Asc(OH)_2 \rightarrow NO + 2NaMal + 2H_2O + AscO_2 \quad (4)$$

EXAMPLE 2

Experimental Procedure for Preparing an Ointment Which Will Slowly Release NO The three components mentioned above, in the same ratios, are admixed with a petroleum-based nonaqueous ointment such as petrolatum Vaseline, forming a thick slurry. When applied topically on the skin, this ointment will slowly release NO with water vapor that permeates trough the nonaqueous medium.

EXAMPLE 3

Experimental Procedure for Preparing a Water-based Gel for Gradual Topical Release of NO The three components of Example 1 are used, but sodium nitrite and maleic acid are kept in separate gels prior to use. A warm solution of sodium nitrite (0.1 mole (1 to 5% concentration) in distilled water is converted into a gel by adding hydroxyethylcellulose (molecular weight 250,000–1, 250,000) or another gel-forming substance such as another cellulose derivative, gelatin or agar, e.g., in such a ratio as to obtain the desired consistency of the gel, and to incorporate all the solution, after 24 h at room temperature. For instance, with 1.6 g of hydroxyethylcellulose with average molecular weight 750,000, one obtains a satisfactory transparent gel with 50 ml solution. Separately, another gel is prepared similarly from distilled water, hydroxyethylcellulose, maleic acid (0.1 moles) and ascorbic acid (0.15–0.2 moles, same concentration as the nitrite). On admixing equal amounts of the two gels immediately before use, placing the mixture on intact skin, and covering it (or not) with an adhesive bandage, NO will be delivered topically. It is preferable (when mixing the two gels is not done or is done on the skin) to have the gel with nitrite in contact with the skin, and to apply the other gel over it, in order to reduce any irritation due to the low pH of the mixture or acid gel. If the two gels have sufficiently high consistency, thin slices of appropriate dimensions from each of the two gels can be cut and sandwiched, separated by an impermeable plastic or metal foil; immediately before use the foil can be removed, the two slices can be slightly pressed against one another and covered by the airtight adhesive bandage, if desired, for gradual topical delivery of NO.

In all cases, care should be exercised in order to minimize or avoid any overdosage of NO or of nitrite. Contact between the atmosphere and the mixture producing nitric oxide is preferably avoided or minimized because, under some conditions, NO may be rapidly oxidized by air (unless extremely diluted) to afford undesirable nitrogen dioxide.

EXAMPLE 4

Wound Healing—Nitrite Reduction/Aloe

Objective: To investigate the effects of Nitric Oxide on a second degree partial thickness burn. Also, to compare the healing rate of NO treatment with that of Aloe vera. The study will include different gels with different concentrations and viscosities.

FIGS. 1–6 present the data from two separate experiments. Both experiments deal with healing of second degree burns on rats as a function of time and treatment methodology.

In both experiments, Sprague Dawley male rats (average weight 275 grams) were anesthetized with 0.025 ml of sodium nebutal. Once under anesthesia, the rats' backs were shaved as close as possible, followed by a treatment of NARE for five minutes to remove any remaining hair.

A rubber pad template with a removed oval section in the center was used to standardize the burn size among the animals. This template was placed over a bath containing 75 degree Celsius water, allowing only a small area of hot water surface area. The anesthetized animal's backs were then pressed against the template for 10 seconds, only being burned by the oval opening. The animals were treated with various applications immediately after being burned. The animals were next allowed to awaken on a heating pad and returned to their cages. In general, wound size increases initially regardless of treatment methodology, as damaged skin sloughs off.

Measurement of wound areas was done directly by tracing the wound on transparent film every two days with areas measured via planimetry. In each experiment, groups of 5 rats were utilized. Thus, the first experiment, with five different groups, was for a total of 25 animals. In the second experiment with nine groups, a total of 45 animals were involved.

The first experiment demonstrating the healing effect of the gel technology utilized the following gels.

$NaNO_2$ Gel: Dissolve 3g $NaNO_2$ in 200 ml distilled water (some heat required). Upon dissolution, add 1.5 grams of hydroxyethyl cellulose gel (MW 720,000).

Acid Gel: Dissolve 7 grams of Vitamin C and 3.3g Maleic acid in 200 ml distilled water. Upon dissolution, add 1.5 grams of hydroxyethyl cellulose (MW 720,000) was dissolved.

Figure 2:
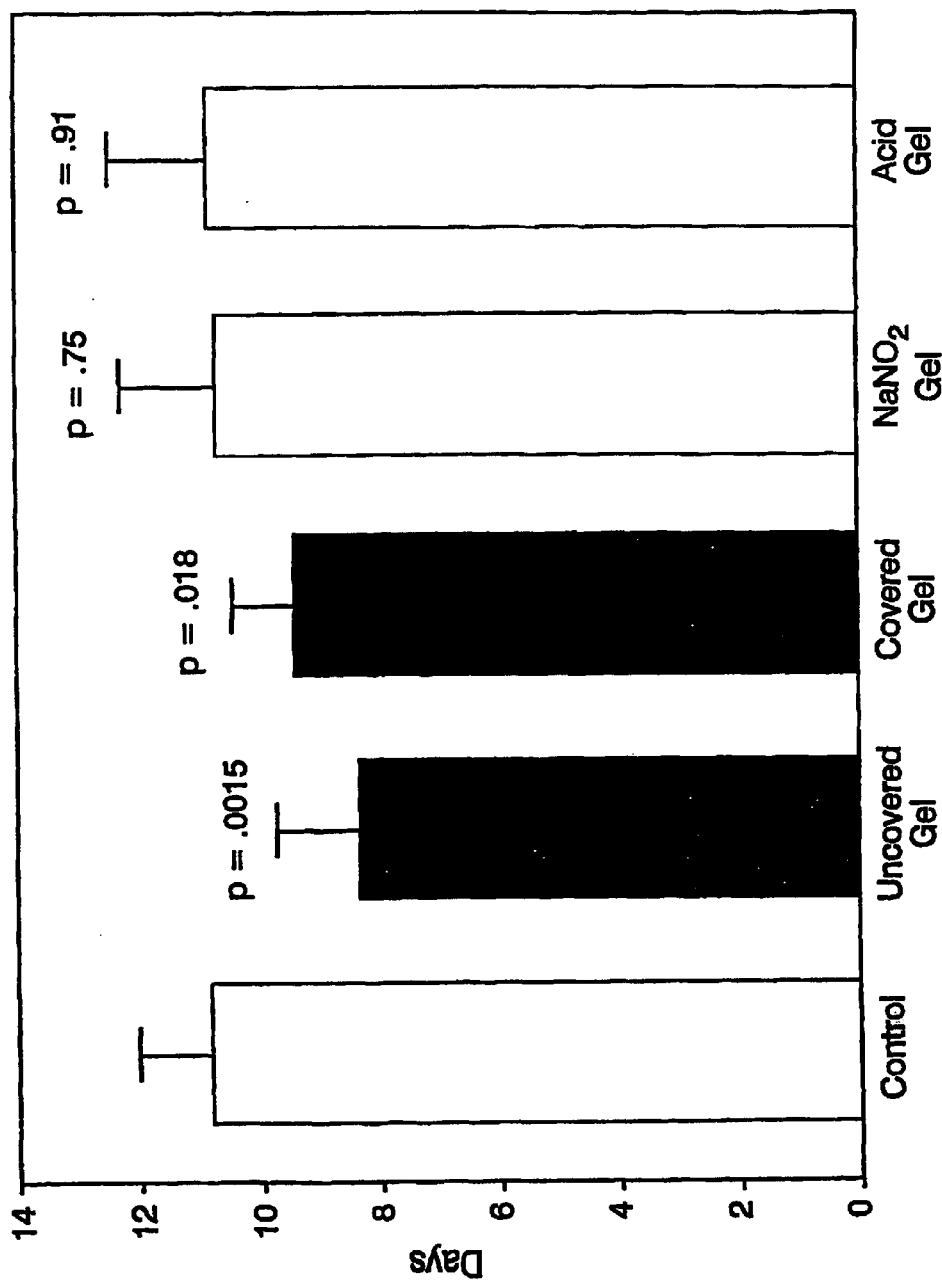
FIG. 2 compares the time to 50% healing from the initial wound size for the experiment of FIG. 1. The error bars and p-values are given. The uncovered gel is statistically shown to be superior to all other methods, with high statistical certainty.
Figure 5:
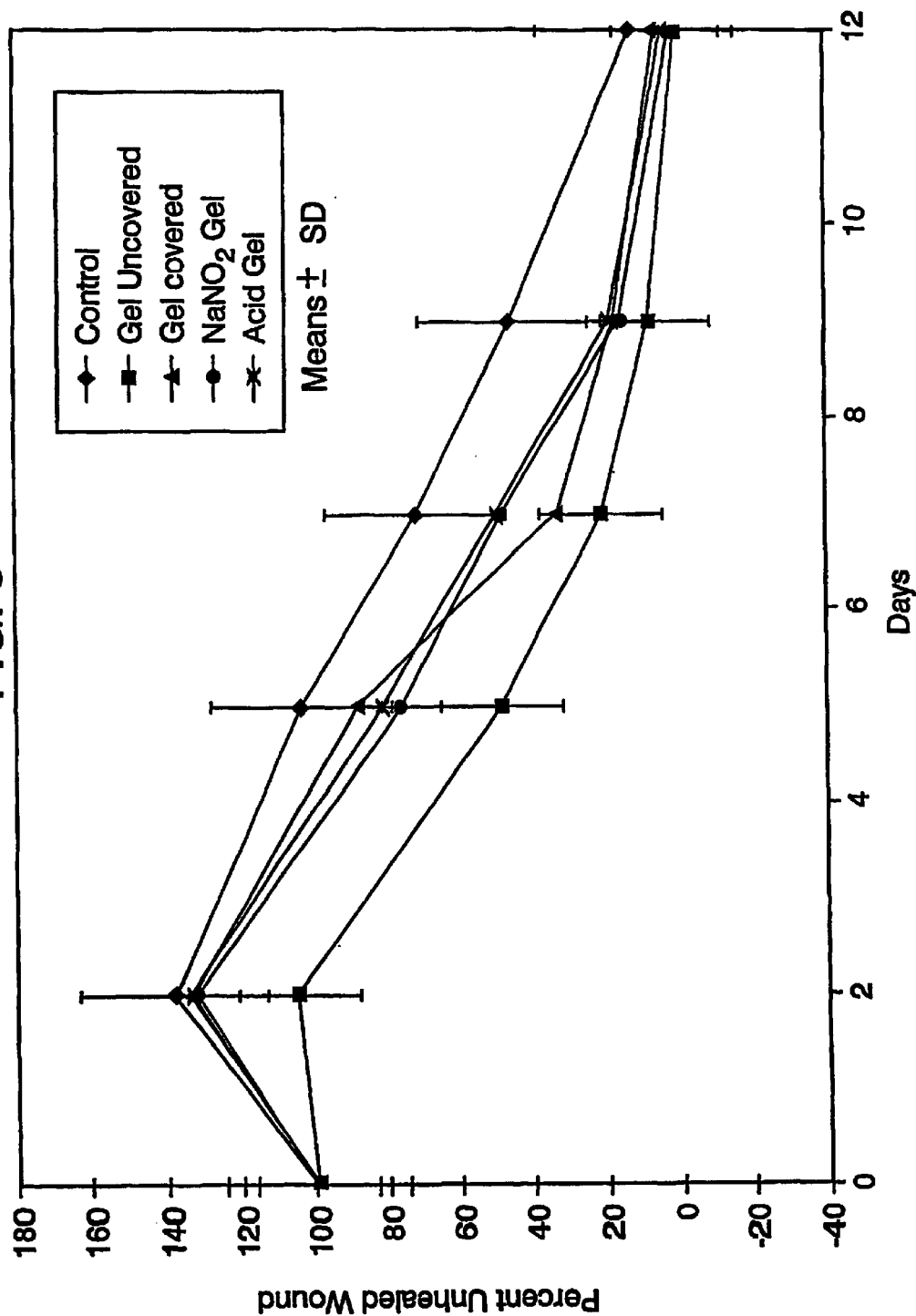
FIG. 5 is for the same experiment as FIGS. 1 and 2 but showing a normalized curve where each wound is normalized to one and the ordinate is the percent remaining unhealed.

The results from the first experiment are shown in FIGS. 1, 2 and 5.

The second experiment investigated modifications of the gels to higher sodium nitrite concentration and higher viscosity compared to the first experiment and also compared healing to Aloe Vera treatments (Dermaide Aloe Cream, Dermaide Research Corp., Ill.). The second experiment also compared treatment frequencies—once (1×) as compared to twice (2×) per day.

To obtain the double viscosity gels, a higher molecular weight hydroxyethyl cellulose (MW 1,300,000) was substituted. To obtain the double nitrite concentration, the $NaNO_2$ concentration was doubled in the sodium nitrite gel (i.e. use 6 g instead of 3).

Figure 3:
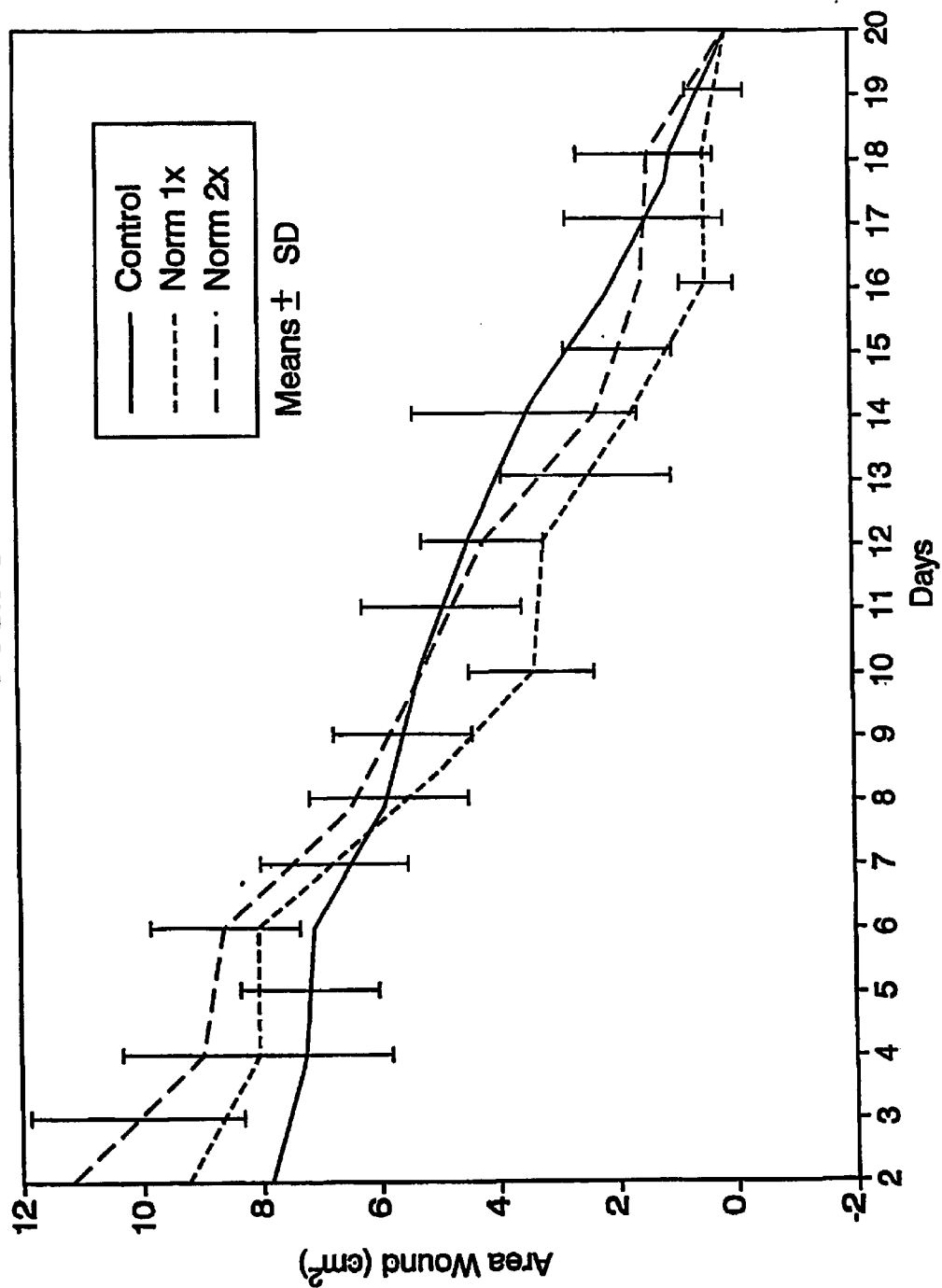
FIG. 3 compares gels releasing NO applied once or twice daily.
Figure 4:
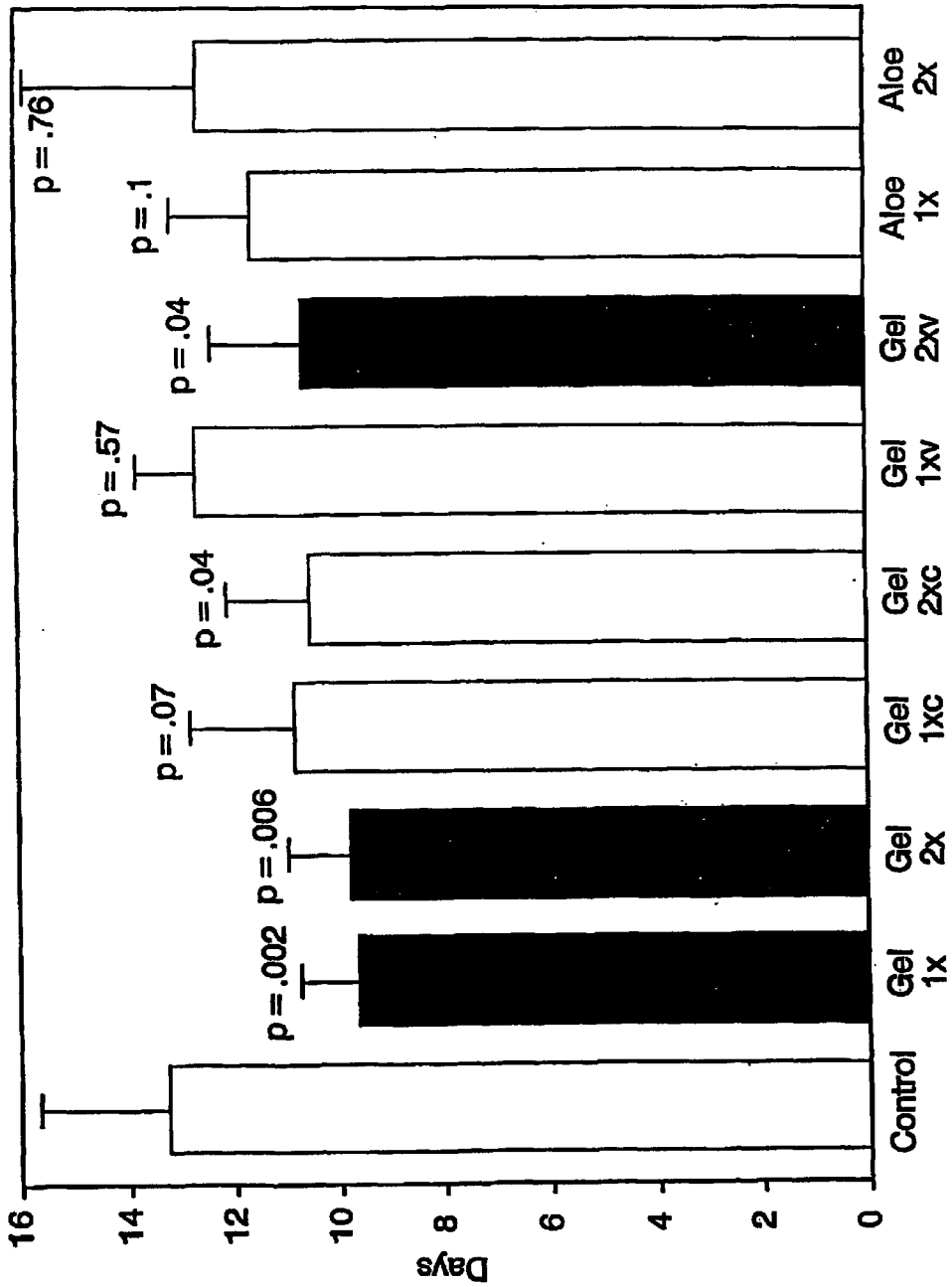
FIG. 4 is as described for FIG. 3 but comparing higher viscosity gels, higher nitrite concentration gels and aloe vera cream. Again, statistical significance is found favoring the gels. The legend means: control, gel treatment once (1×) per day, gel twice (2×) per day, regular (1XC) or concentrated (2XC) nitrite gel once per day, a normal nitrite concentration (1XV) or more viscous gel (2XV) per day, and finally aloe vera at two viscosities.
Figure 6:
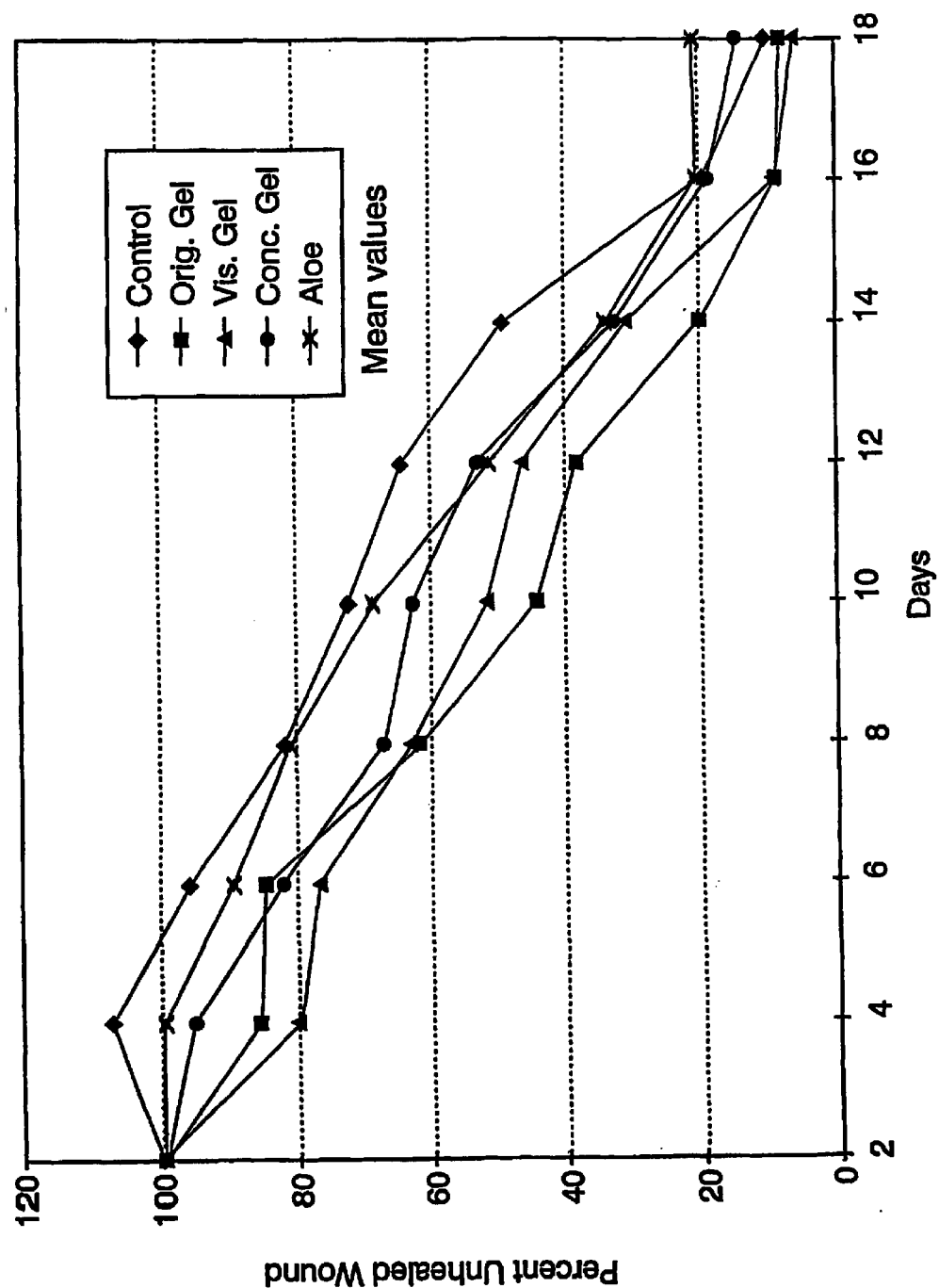
FIG. 6 is a normalized curve for the experiment in FIGS. 3 and 4.
Figure 7:
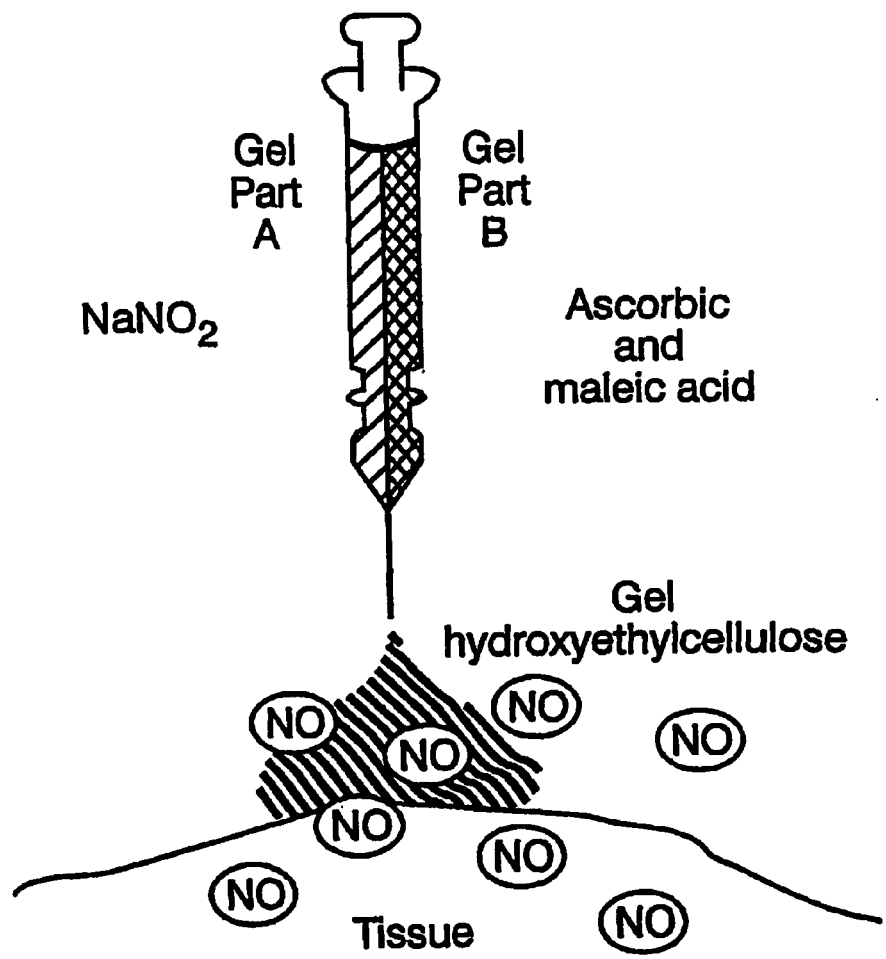
FIG. 7 schematically shows a two ported injection device for administering a nitrite gel and acid gel for mixture and application to a body site.

The results from the second experiment are shown in FIGS. 3, 4 and 6. In all cases, the gels are preferably sealed after forming.

FIG. 1 gives the raw data for healing of second degree burns comparing control with covered and uncovered mixed gels (which release NO) and the individual acid or nitrite gels. The result demonstrates that healing efficacy is the result of the NO released as opposed to the components in the individual gels. The uncovered and covered gels which release NO clearly heal faster in absolute terms.

FIG. 2 compares the time to ½ healing from the initial wound size for the first experiment. The error bars and p-values are given. The uncovered acid-nitrite gel is statistically shown to be superior to all other methods with high statistical certainty (followed by the covered acid-nitrite gel).

FIG. 3 compares once and twice daily gel applications. Both applications caused more rapid healing than controls.

FIG. 4 shows healing ½ time but this time comparing higher viscosity gels, higher nitrite concentration gels and aloe vera creams. Again, statistical significance is found favoring the No producing gels. The legend means: control, gel treatment once (1×) per day, gel twice (2×) per day, nitrite concentration gel (1XC) and twice concentrated (2XC), a normal nitrite concentration but normally viscous gel (1XV) and more viscous gel (2XV) once per day, and finally aloe vera once or twice per day.

FIG. 5 is for the same experiment as FIGS. 1 and 2 but showing a normalized curve where each wound is normalized to one and the ordinate is the percent remaining unhealed.

FIG. 6 is a normalized curve for experiment two shown in FIGS. 3 and 4.

EXAMPLE 5

Note on Biological Tests to Date

These tests indicate efficacy of gel treatments for wound healing. This is, however, just one of the applications of the technology. The present invention demonstrates that the systems described herein release NO, and also that they produce increased local blood flow.

That observation is independent of these burn experiments and certainly makes the discovery applicable in any case where increased local blood circulation can be therapeutic.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following and earlier listed references, to the extent that they provide exemplary procedural or other details supplementary to those set forth herein, are specifically incorporated herein by reference.

Butler and Williams, *Chem. Soc. Revs.*, 22:233, 1993

Cornforth, *In: Nitric Oxide. Principles and Actions*, Ed. J. Lancaster Jr., Academic Press, San Diego, p. 259, 1996.

Feelisch and Stamler, (Eds.), "Methods in Nitric Oxide Research," Wiley, New York, 1996

Feelisch and Stamler, *In: Methods in Nitric Oxide Research*, Eds. M. Feelisch and J. S. Stamler, Wiley, p 0.71, namely p 0.102, 1996.

Garfield, Balaban, Seitz, Klein, Lesko, U.S. patent application Ser. No 0.08/440,970, May 15, 1995.

Garfield, Balaban, Seitz, U.S. patent application Ser. No. 08/633,337, Apr. 17, 1996.

Hansen, Croisy, Keefer, *In: N-Nitroso Compounds: Occurrence and Biological Effects* (Eds. Bartsch, H., O'Neill, I. K., Castegnaro, M. and Okada, M.), International Agency for Research on Cancer Publication No. 41, Lyon, p. 21, 1992

Ignarro and Murad, (Eds.), "Nitric Oxide. Biochemistry, Molecular Biology, and Therapeutic Implications", *Advances in Pharmacology*, Academic Press, San Diego, 1995.

Keefer, Christodolou, Dunams, Hrabie, Maragos, Saavedra, Wink, *In: Nitrosamines and Related N-Nitroso Compounds: Chemistry and Biochemistry*, (Eds. R. N. Loeppky and C. J. Michedja), ACS Symp. Series No. 553, *Amer. Chem. Soc.*, Washington, D.C., p. 136–146, 1994

Keefer, Nims, Davies, Wink, D. A., *Methods in Enzymology*, 268:281, 1996.

Keefer, Wink, Dunams, Hrabie, U.S. Pat. No. 5,212,204 (May 18, 1993); *Chem. Abstr*, 113:145344, 1990 for Pat Appl. 423,279 (Mar. 1, 1990)

Lancaster, (Ed.), "Nitric Oxide. Principles and Actions", Academic Press, New York, 1996

Mirvish, *Appl. Pharmacol.*, 31:325, 1975.

Moncada, Marletta, Hibbs, Feelisch, Busse, (Eds.), "The Biology of Nitric Oxide", vols. 1–4, Portland Press, Colchester, 1992–1994

Reith and Szakali *J. Food Sci.*, 32:188, 194, 1967.

Smith et al.,(U.S. Pat. No. 5,519,020), issued May 21, 1996.

USDA *Federal Registry*, Washington, D.C., 43:20992, 1978.

Vincent, (Ed.), "Nitric Oxide in the Nervous System", Academic Press, New York, 1995

Williams, *Chem. Soc. Revs.*, 25:77–84, 1996

What is claimed is:

1. A method for therapeutically applying NO, the method comprising combining a nitrite salt, a biocompatible reductant and an acid with a pKa between about 1 and about 4 in a medium and topically applying said combination to a body site.

2. A method for topical delivery of nitric oxide (NO) comprising mixing a powdered nitrite salt with a powdered reductant and an acid having a pKa between about 1 and about 4 in a diffusion-inhibiting topically applicable medium and topically applying an effective amount of said mixture to a body site.

3. The method of claim 1 or 2 where the reductant is an ascorbate salt, an erythrobate or α-tocopherol.

4. The method of claim 1 or 2 where the reductant is ascorbic acid.

5. The method of claim 1 or 2 where the acid is an organic acid.

6. The method of claim 1 or 2 where the acid is maleic acid.

7. The method of claim 1 or 2 where the acid is an inorganic acid.

8. The method of claim 1 or 2 where the nitrite salt is an inorganic salt.

9. The method of claim 1 or 2 where the nitrite salt is sodium nitrite.

10. The method of claim 1 or 2 where the medium is an aqueous gel.

11. The method of claim 1 or 2 where the medium comprises hydroxyethyl cellulose or poloxama.

12. The method of claim 1 or 2 where the medium is an organic salve.

13. A topically applicable ointment for controlled NO delivery comprising a nitrite salt, a reductant and an acid with a pKa between about 1 and about 4 in a medium sufficiently viscous to inhibit diffusion, permit slow NO release and facilitate topical application.

14. The ointment of claim 13 where the reductant is ascorbic acid, an ascorbate salt, an erythrobate or α-tocopherol.

15. The ointment of claim 13 where the reductant is ascorbic acid.

16. The ointment of claim 13 where the acid is an organic acid.

17. The ointment of claim 13 where the acid is maleic acid.

18. The ointment of claim 13 where the acid is an inorganic acid.

19. The ointment of claim 13 where the nitrite salt is an inorganic salt.

20. The ointment of claim 13 where the nitrite salt is sodium nitrite.

21. The ointment of claim 13 where the medium is an aqueous gel.

22. The ointment of claim 13 where the medium is an organic salve.

23. A composition for generating and controlling the release rate of NO for topical applications comprising a first aqueous gel and a second aqueous gel, the first gel comprising a nitrite salt, and the second gel comprising an acid having a pKa between about 1 and about 4 and at least one of the first and second gel comprising a reductant.

24. The composition of claim 23 where the reductant is ascorbic acid, an ascorbate salt, an erythrobate or α-tocopherol.

25. The composition of claim 23 where the reductant is ascorbic acid.

26. The composition of claim 23 where the acid is an organic acid.

27. The composition of claim 23 where the acid is maleic acid.

28. The composition of claim 23 where the acid is an inorganic acid.

29. The composition of claim 23 where the nitrite salt is an inorganic salt.

30. The composition of claim 23 where the nitrite salt is sodium nitrite.

31. A method for delivering the two gels of the composition of claim 23 from a single container with two separate chambers by forcing them through a nozzle with a hole for each chamber.

32. A method for topical application of the gels of the composition of claim 23 in layers, with the nitrite-containing gel layer being in contact with the skin, the second gel layer being separated from the first by an impermeable plastic or metal foil until just before use, when the plastic or foil is removed, and the gel layers are topically applied.

33. A method in which the ointment of claim 13 or the two gels of the composition of claim 23 are applied on the skin through an interposed gas-permeable membrane for lessening any skin irritation.

34. A gel comprising a nitrite salt, an acid with a pKa between 1 and 4, and a reductant, for medical use.

35. A kit containing a first gel comprising a nitrite salt, a second gel comprising an acid with a pKa between 1 and 4, and a reductant in at least one of the first and second gels.

* * * * *

Adverse Decisions in Interference

Patent No. 7,048,951, William A. Seitz, Robert E. Garfield, Alexandru T. Balaban and Randall J. Stewart, SYSTEMS AND METHODS FOR TOPICAL TREATMENT WITH NITRIC OXIDE, Interference No. 105,687, final judgment adverse to the patentees rendered November 24, 2009, as to claims 1-35.

*(Official Gazette, July 27, 2010)*